United States Patent [19]

Knapp

[11] Patent Number: 4,803,051

[45] Date of Patent: Feb. 7, 1989

[54] ATOMIC SPECTROMETER APPARATUS

[75] Inventor: Günter Knapp, Graz, Austria

[73] Assignee: Bodenseewerk Perkin-Elmer & Co., GmbH, Überlingen, Fed. Rep. of Germany

[21] Appl. No.: 868,204

[22] Filed: May 23, 1986

Related U.S. Application Data

[63] Continuation of Ser. No. 472,394, Mar. 4, 1983, abandoned, which is a continuation of Ser. No. 320,626, Nov. 12, 1981, abandoned.

[30] Foreign Application Priority Data

Nov. 12, 1980 [DE] Fed. Rep. of Germany ....... 3042907

[51] Int. Cl.$^4$ ............................................. G01N 21/72
[52] U.S. Cl. ....................................... 422/80; 356/315; 422/68; 422/78; 436/73; 436/171; 436/178; 436/181
[58] Field of Search ...................... 422/54, 69, 70, 78, 422/80, 81, 88, 89, 83, 99, 101, 68; 436/73, 161, 177, 178, 181, 171; 210/198.2, 656, 670, 684, 688; 423/89, 24, 100, 139, 508, DIG. 14; 356/315

[56] References Cited

U.S. PATENT DOCUMENTS

| | | | |
|---|---|---|---|
| 3,095,278 | 6/1963 | Green | 422/54 |
| 3,585,003 | 6/1971 | Scolnick | 422/54 |
| 3,661,527 | 5/1972 | Eggertsen et al. | 422/54 X |
| 3,700,416 | 10/1972 | Lucid | 423/139 X |
| 3,728,257 | 4/1973 | Fuxelius | 210/684 X |
| 3,873,581 | 3/1975 | Fitzpatrick et al. | 210/688 X |
| 3,888,124 | 6/1975 | Campbell et al. | 55/72 X |
| 3,933,431 | 1/1976 | Trujillo et al. | 436/76 |
| 3,939,071 | 2/1976 | Katzakian, Jr. et al. | 210/674 |
| 3,969,244 | 7/1976 | Kobayashi et al. | 210/688 |
| 3,988,919 | 11/1976 | Talmi et al. | 55/67 X |
| 4,023,929 | 5/1977 | Becker et al. | 422/78 |
| 4,029,583 | 6/1977 | Ho Chang et al. | 55/386 X |
| 4,065,502 | 12/1977 | MacKay et al. | 423/100 X |
| 4,066,402 | 1/1978 | Komiyama et al. | 422/78 |
| 4,116,836 | 9/1978 | DeAngelis | 55/386 X |
| 4,175,037 | 11/1979 | Benney et al. | 55/67 X |
| 4,230,665 | 9/1980 | Huber | 422/69 |
| 4,277,251 | 7/1981 | Leichnitz | 422/88 X |
| 4,287,752 | 9/1981 | Ury | 73/23.1 |
| 4,293,415 | 10/1981 | Bente et al. | 55/386 X |
| 4,346,055 | 8/1982 | Murphy et al. | 422/54 |
| 4,404,288 | 9/1983 | Huber | 436/177 |

FOREIGN PATENT DOCUMENTS

| | | | |
|---|---|---|---|
| 0350508 | 6/1979 | Austria . | |
| 3233130 | 3/1984 | Fed. Rep. of Germany | 356/315 |
| 0068965 | 6/1976 | Japan | 210/688 |
| 0004354 | 1/1978 | Japan | 210/688 |
| 7117773 | 6/1972 | Netherlands | 210/688 |
| 0625051 | 8/1981 | Switzerland | 422/88 |
| 0741384 | 4/1975 | U.S.S.R. | 210/670 |
| 1251049 | 9/1971 | United Kingdom . | |
| 1312583 | 4/1973 | United Kingdom . | |

OTHER PUBLICATIONS

Preconcentration Of Trace Metals using Chelating Groups Immobilized via Silylation, Leyden et al., Analytical Chemistry vol. 47, pp. 1612–1617 3-heptone vs. 4-methyl-2-pentanone as Extracting Solvents in Atomic Absorption Spectrophotometry.

(List continued on next page.)

Primary Examiner—Barry S. Richman
Assistant Examiner—Robert J. Hill, Jr.
Attorney, Agent, or Firm—Ronald G. Cummings; Edwin T. Grimes; Francis L. Masselle

[57] ABSTRACT

An atomic spectrometer in combination with an atomizer apparatus for atomizing a test sample into an atomic state for analysis in the atomic spectrometer. The atomizer apparatus includes a heater for heating a sample to free individual atoms of the sample for atomic spectroscopy, a tube member containing a packing of an adsorbent, a reagent adsorbed on the adsorbent which reacts with a metal constituent in a sample to form a metal complex which adsorbs to the adsorbent at a first temperature and is volatile at a second higher temperature for desorption from the adsorbent, and a heater for heating the tube member.

12 Claims, 1 Drawing Sheet

OTHER PUBLICATIONS

Everson et al., Analytical Chemistry, vol. 46, pp. 2040-2042.
Knapp et al., Chemical Abstracts, vol. 95, Abstract No. 95:2845q, Jul. 6, 1981.
Tavlaridis et al., Z. Anal. Chem., vol. 282, pp. 17-19, 1976.
Rodriguez-Vazquez, Anal. Chim. Acta, vol. 73, pp. 1-32, 1974.
"Metals Analyzed by Gas Chromatography", Chemical and Engineering News, Jul. 1, 1963, p. 41.
"Gas Chromatography Splits Metal Chelates", Chemical and Engineering News, Apr. 2, 1962, p. 50.
Krupcik et al., J. of Chromatography, vol. 112, pp. 189-196, 1975.
Kantor et al., Talanta, vol. 23, No. 8, pp. 585-586, 1976.
Jarrell-Ash Atomic Absorption/Flame Spectrometer Product Information, 1965.
Knapp, Anal. Chim. Acta, vol. 77, pp. 293-297, 1975.

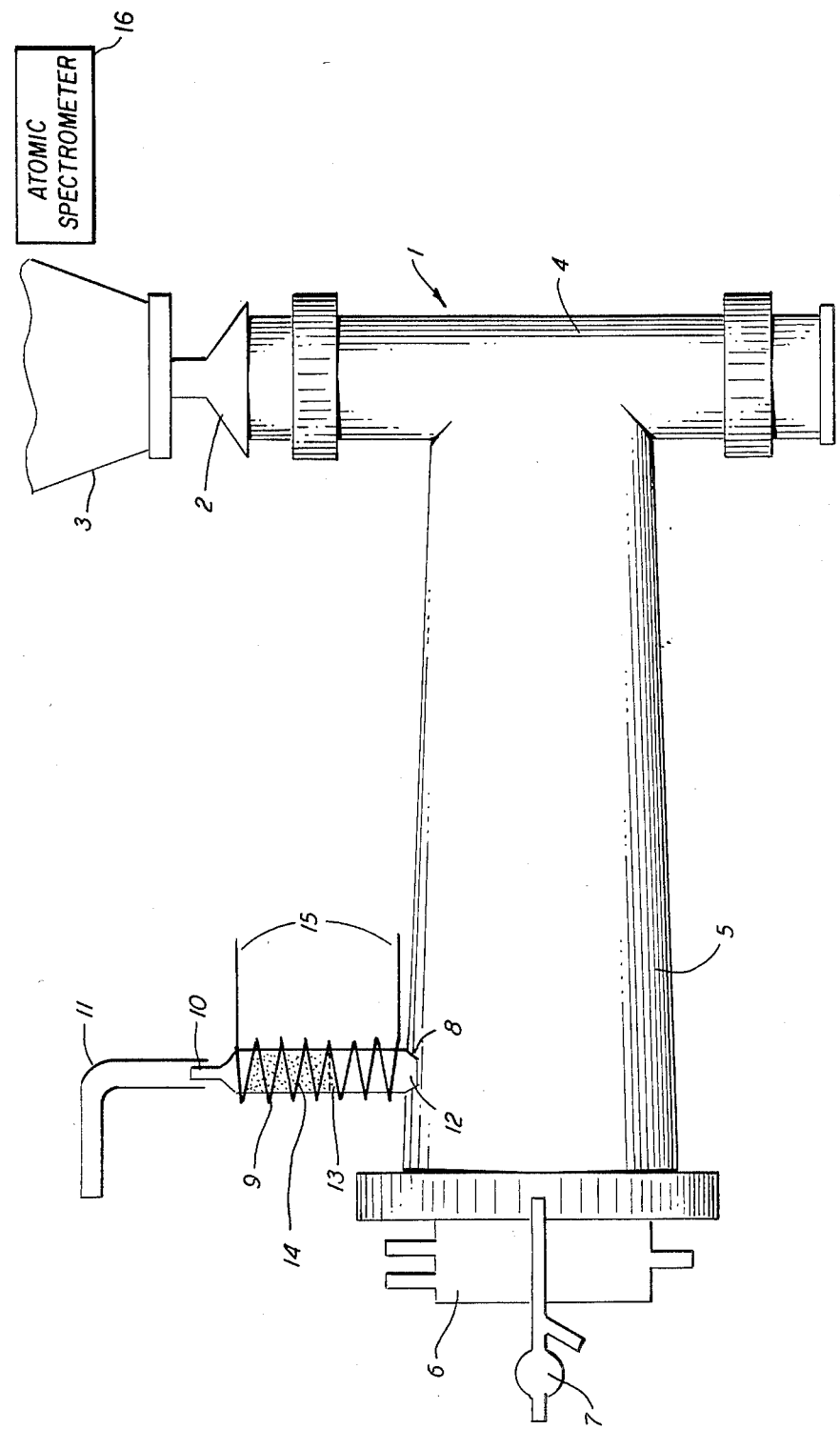

ATOMIC SPECTROMETER APPARATUS

BACKGROUND OF THE INVENTION

This application is a continuation of U.S. application Ser. No. 472,394, filed on Mar. 4, 1983, now abandoned, which in turn is a continuation of U.S. application Ser. No. 320,626, filed Nov. 12, 1981, now abandoned.

The present invention generally relates to a method for forming a gaseous sample and, in particular, relates to such a method which includes reacting a sample material with a chemical reagent. The present invention further relates to an apparatus for carrying out the aforesaid method.

Atomic spectroscopy, e.g. atomic absorption spectroscopy or atomic emission spectroscopy, is often employed to accurately determine the concentration of a particular element in a sample material. One mechanism employed in atomic spectroscopy converts the sample material, which is normally an aqueous solution, to a gas, which is then fed into a burner wherein atomizations of the gas takes place. The atomized gas is then used either as an absorber or an emitter and the concentration of the caught element therein determined.

When the presence of rather small quantities of various elements, e.g. mercury, arsenic, antimony or selenium, is sought, the aqueous solution is usually subjected to a chemical reaction to produce a concentrated hydride thereof which is subsequently isolated and measured. Such a procedure is described in U.S. Pat. Nos. 4,138,215 and 4,268,478. The detection sensitivity of an analysis is significantly increased by utilization of such a technique. However, the usefulness of forming hydrides is limited in the number of elements capable of being so enriched.

SUMMARY OF THE INVENTION

Accordingly, it is one object of the present invention to provide a method, as well as an apparatus, for carrying out such a method, by means of which an improvement in the limit of detection is achievable for a greater number of elements. In particular, this object is directed to include elements which do not form volatile hydrides.

This object is achieved, at least in part, by a method including the steps of reacting a sample material with a complex forming reagent to generate metal complexes which are volatile at higher temperatures, adsorbing those metal complexes and subsequently desorbing those complexes at a higher temperature.

Another object of the present invention is to provide an apparatus via the use of which the aforesaid method can be performed in combination with an atomic spectrometer.

This object is accomplished, at least in part, by an apparatus including an open tube member having a packing of an adsorbent material and including means for heating the tube member to an appropriate temperature whereat desorption takes place.

In accordance with the present invention, metal ions present in the solution of the sample material are bound in complexes which are separated by adsorption from the remaining components present in the solution. Subsequently, the volatile complexes are desorbed at increased temperature and entrained in a flow of inert gas transferring the same to the atomizer of the analytical apparatus. Depending on the selected complex forming agent, many elements can be separated more or less selectively from the solution of the sample material in a highly simple manner and subjected to analytical determination. Thereby, high enrichments are achieved and the detection sensitivity is considerably increased.

Advantageously, the complex forming reagent is adsorbed to an adsorbent, preferably hydrophobic silica gel, and the sample material solution is reacted with the adsorbent loaded with the complex forming reagent in the method according to the invention.

Conveniently, a dithiocarbamate, for example diethylammonium diethyldithiocarbamate, or, respectively, a 1.3-diketone, for example, trifluoroacetyl acetone, is used as a complex forming reagent.

Other objects and advantages will become apparent to one skilled in the art from the following detailed description and drawing.

Brief Description of the Drawing

The single FIGURE of the drawing, not drawn to scale, is an illustration of an apparatus embodying the principles of the present invention.

DETAILED DESCRIPTION OF THE INVENTION

In the drawing, an atomizer of an atomic absorption spectrometer 16 is schematically illustrated in the form of a burner 1 which includes a suitably designed head 2 and a flame 3. The apparatus further includes a gas feeder 5 opening into the side of a burner tube 4, a burning gas feeding means 6 and a sprayer 7 for supplying a liquid sample being connected to the gas feeder 5.

A tube member 9 is inserted into a lateral insertion aperture 8 formed in the wall of the gas feeder 5. Tube member 9 has a first end forming a connector 10, which is connected to a source of inert gas (for example, argon, nitrogen), not shown, through a connecting line 11, and preferably has a conically tapering second end 12 which is adapted to fit into the insertion aperture 8. The tube member 9 is preferably manufactured from quartz glass; above a glass frit plate 13 therein is contained a packing 14 comprising an adsorbent at which metal complexes of diethylammonium diethyldithiocarbamate are adsorbed. Heating means forming a heater coil 15 and adapted to be connected to a current source (not shown) surround the tube member 9.

EXAMPLE

A tube member 9 made of quartz glass tubing having a width of about 2 mm is charged with a 40 mm high packing 14 of hydrophobic silica gel (Chromosorb W-DMCS) above glass frit plate 13; subsequently, a solution of 50 mg diethylammonium diethyldithiocarbamate in 400 ul of an organic solvent is placed on the column. Thereafter, the column is washed with 1 ml of distilled water. Hydroxylammonium chloride is added as an anti-oxidant to 25 ml of a solution of a sample material containing metal salts and the solution is run through the column which is subsequently washed with 1 ml of distilled water.

The tube member 9 is then inserted into the insertion aperture 8 of gas feeder 5 and connected to connecting line 11. After starting the supply of burning gas and igniting burner 1, the analytical apparatus is properly set and the current supply to heater coil 15 is energized. At an appropriately high temperature, the metal complexes become desorbed by the flow of inert gas entering via connecting via 11 and passing through the packing 14 without the inert gas affecting the operation of burner 1. The complexes thus enter the flame 3 of burner 1 and become thermally decomposed therein so that their atomic absorption can be measured.

The method has been successfully performed in the analytical determination of lead, cadmium, cobalt, copper, nickel, selenium and zinc.

With proper adaptation, which adaptations will be readily apparent from respective apparatus conditions, the tube member 9 can be combined analogously with analytical apparatus measuring atomic emission using a plasma torch as an atomizer.

The tube member 9 should have an internal width in the range of 1 mm to 5 mm and an effective length in the range of 30 mm to 100 mm. The hydrophobic silica gel may be replaced with any other hydrophobic carrier material known in the field of chromatography. Furthermore, other complex forming reagents forming volatile complexes like 1.3-diketones may be used successfully.

In the example hereinbefore described, the complex forming reagent is adsorbed at the adsorbent and the solution of the sample material is reacted with the adsorbent loaded with the complex forming reagent. Alternately, the complex forming reagent is added to a solution of the sample material and the complex formed thereby are then adsorbed at the adsorbent from the reaction mixture.

The specific embodiment described above is exemplary in purpose only and is not deemed as being limiting. The present invention is limited and defined only by the appended claims and the reasonable interpretation thereof.

What is claimed is:

1. In combination, an atomic spectrometer and an atomizer apparatus for atomizing a test sample into an atomic state for analysis in said atomic spectrometer, wherein said atomic spectrometer is operatively connected to said atomizer apparatus such that said atomic spectrometer is capable of analyzing an atomized test sample produced by said atomizer apparatus, and wherein said atomizer apparatus comprises:

means for heating a sample to free individual atoms thereof for atomic spectroscopy, said heating means having an inlet opening for connection to a tube member for inletting a sample into said heating means;

a tube member containing a packing of an adsorbent for adsorbing predetermined metal complexes which adsorb to the adsorbent at a first temperature and are volatile at a second higher temperature for desorption from said adsorbent, said tube member having an inlet port for introducing a sample to said adsorbent, an outlet port connected to the inlet opening of the heating means and means for connecting the tube member to a source of carrier gas for carrying metal complexes desorbed from the adsorbent to the heating means;

a reagent for reacting with a selective metal constituent of a sample to form a predetermined metal complex which adsorbs to the adsorbent at a first temperature and is volatile at a second higher temperature for desorption from said adsorbent, wherein said reagent is adsorbed on said adsorbent in said tube member so that a sample may be introduced to said adsorbent to form metal complexes with said reagent; and tube heating means disposed about said tube member for selectively heating said packing and any adsorbed metal complexes thereat to a temperature to desorb any such metal complexes therefrom for entraining into a flow of carrier gas through said tube member to said heating means for atomization thereof.

2. The apparatus of claim 1 wherein said heating means comprises a burner tube, a head mounted on an end of said burner tube arranged for a flame to emit therefrom, means defining a gas feeder opening into a side of said burner tube, means for feeding burner gas to said gas feeder opening and wherein said inlet opening is a lateral insertion inlet opening in a wall of the feeding means, said tube member being laterally insertable into said inlet opening.

3. The apparatus of claim 1 wherein said tube member is fabricated from quartz glass.

4. The apparatus of claim 1 wherein said reagent is diethylammonium diethyldithiocarbamate.

5. The apparatus of claim 1 wherein said reagent is 1.3 diketone.

6. The apparatus of claim 1 wherein said heating means comprises a heating coil mounted about said tube member.

7. The apparatus of claim 1 wherein said tube member has a width of from between about 1 mm to about 5 mm and an effective length of from about 30 mm to about 100 mm.

8. The apparatus of claim 1 wherein a frit plate is mounted within said tube member between said inlet and outlet ports with said packing being disposed between said frit plate and said inlet port.

9. The apparatus of claim 1 further comprising means for readily detachably mounting said tube member to said inlet opening of said heating means to permit metal complexes to be adsorbed at said adsorbent and said packing to be thereafter washed while said tube member is detached from said heating means and to permit desorption of such metal complexes from said adsorbent while said tube member is mounted to said heating means.

10. The apparatus of claim 9 wherein said tube member has opposite inlet and outlet ends, said inlet end being adapted for connection to a source of carrier gas and said outlet end being conically tapered for insertion into the inlet opening of said heating means.

11. IThe apparatus of claim 1 wherein said adsorbent is a hydrophobic carrier material.

12. The apparatus of claim 11 wherein said hydrophobic carrier material is silica gel.

* * * * *